United States Patent [19]

Känel et al.

[11] Patent Number: 5,256,815
[45] Date of Patent: Oct. 26, 1993

[54] BISULFITE ADDUCTS OF 2,4-DIHALOBUTRALDEHYDE

[75] Inventors: Hans-Ruedi Känel, Bubendorf; John G. Dingwall, Nuglar, both of Switzerland

[73] Assignee: Ciba-Geigy Corporation, Ardsley, N.Y.

[21] Appl. No.: 975,035

[22] Filed: Nov. 12, 1992

Related U.S. Application Data

[62] Division of Ser. No. 575,458, Aug. 30, 1990, Pat. No. 5,189,227, which is a division of Ser. No. 472,677, Jan. 30, 1990, Pat. No. 4,968,836.

[30] Foreign Application Priority Data

Feb. 2, 1989 [CH] Switzerland ............... 365/89

[51] Int. Cl.$^5$ ................................. C07C 317/18
[52] U.S. Cl. ................................. 562/108; 562/113; 568/32
[58] Field of Search ............ 562/108, 113; 568/32

[56] References Cited

U.S. PATENT DOCUMENTS

| | | | |
|---|---|---|---|
| 2,840,501 | 6/1958 | Meuli .................... | 562/108 |
| 3,239,560 | 3/1966 | Cambre et al. ........ | 562/108 |
| 3,721,711 | 3/1973 | Maravetz .............. | 260/566 |

FOREIGN PATENT DOCUMENTS 0243313 10/1987 European Pat. Off.
2120908 11/1971 Fed. Rep. of Germany.

*Primary Examiner*—C. Warren Ivy
*Assistant Examiner*—Ba K. Trinh
*Attorney, Agent, or Firm*—Marla J. Mathias; Kevin T. Mansfield

[57] ABSTRACT

The invention relates to a process for the preparation of cyclopropanecarbaldehydes of formula

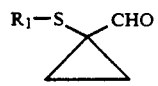
(I)

in which $R_1$ is $C_1$-$C_4$alkyl or benzyl, which comprises
a) reacting a tetrahydrofuran of formula

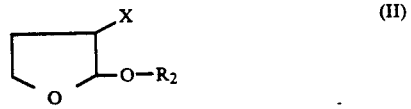
(II)

with a halogenating agent to form a 1,2,4-trihalobutyl ether of formula

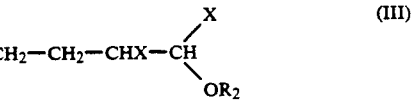
(III)

in which X is halogen and $R_2$ is unsubstituted or halo-substituted $C_1$-$C_{10}$alkyl, $C_3$-$C_6$cycloalkyl that is unsubstituted or substituted by halogen, $C_1$-$C_4$alkyl or by $C_1$-$C_4$alkoxy, or phenyl or benzyl each of which is unsubstituted or substituted by halogen, $C_1$-$C_4$alkyl, $C_1$-$C_4$alkoxy, nitro or cyano, and
b) then reacting the compound of formula III with an aqueous bisulfite solution to form a bisulfite adduct of formula

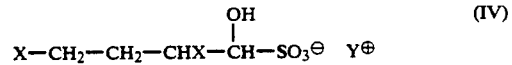
(IV)

in which X is halogen and Y is a cation equivalent of an alkali metal or alkaline earth metal ion, and
c) then cyclising the adduct, in the presence of a base, with a thiolate of formula

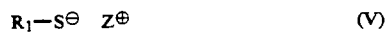
(V)

in which $R_1$ is $C_1$-$C_4$alkyl or benzyl and Z is a cation equivalent of an alkali metal or alkaline earth metal ion, to form a cyclopropanecarbaldehyde of formula I, and to the individual Process of Steps a), b) and c) and the combinations thereof a)+b) and b)+c), and to the novel intermediates of formulae III and IV.

2 Claims, No Drawings

BISULFITE ADDUCTS OF 2,4-DIHALOBUTRALDEHYDE

This is a divisional of Ser. No. 575,458, filed Aug. 30, 1990, now U.S. Pat. No. 5,189,277, which is a divisional of Ser. No. 472,677, filed Jan. 30, 1990, now U.S. Pat. No. 4,968,836.

The invention relates to a novel for the synthesis of 1-alkylthio- and 1-benzylthio-substituted cyclopropanecarbaldehydes of formula

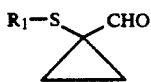   (I)

in which $R_1$ is $C_1$-$C_4$alkyl or benzyl.

The cyclopropanecarbaldehydes of formula I are valuable intermediates for the synthesis of agrochemical active substances. They are valuable, for example, for the preparation of the cycloalkanecarbaldoxime carbamates known from DE-A-21 20 908 and for the synthesis of the 2-acyl-cyclohexane-1,3-diones having herbicidal and plant growth-regulating activity described in EP-A-O 243 313.

Those cyclohexanediones are substituted inter alia in position 5 by a 1-alkylthio- or a 1-benzylthio-cycloprop-1-yl radical. They may be prepared by a malonic ester synthesis starting from 1-alkythio- or 1-benzylthio-cyclopropanecarboxaldehydes, respectively. In that process, first of all the aldehyde is condensed with acetone to form the corresponding 4-(1-alkyl-(or benzyl)-thio)-cyclopropyl-but-3-en-2-one which is subsequently cyclised to form the cyclohexandione using malonic ester or cyanoacetic acid ester. The cyclohexanedione obtainable in this manner is then fuctionalised in position 2 in in a manner known per se.

A process for the preparation of compounds of formula I in which $R_1$ is $C_1$-$C_4$alkyl is known from DE-A-2 120 908. In that five-step process, chloroacetonitrile is reacted by way of alkylthioacetonitrile to form a 1-alkylthicyclopropanecarbonitrile. That compound is then hydrolysed, converted first into the acid chloride and then into an amide, and reduced to the aldehyde by means of $LiAlH_4$.

This process has numerous disadvantages. Apart from the poor total yield of the process, complex process steps are necessary for the individual stages of the reaction. Moreover, the alkylthioacetonitrile required as starting compound is corrosive and irritating to the eyes.

In contrast to that process, the invention relates to a process for the preparation of cyclopropanecarbaldehydes of formula

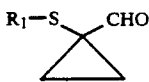   (I)

in which $R_1$ is $C_1$-$C_4$alkyl or benzyl, which comprises
a) reacting a tetrahydrofuran of formula

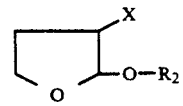   (II)

in which X is halogen and $R_2$ is unsubstituted or halo-substituted $C_1$-$C_{10}$alkyl, $C_3$-$C_6$-cycloalkyl that is unsubstituted or substituted by halogen, $C_1$-$C_4$alkyl or by $C_1$-$C_4$alkoxy, or phenyl or benzyl each of which is unsubstituted or substituted by halogen, $C_1$-$C_4$alkyl, $C_1$-$C_4$alkoxy, nitro or cyano, with a halogenating agent to form a 1,2,4-trihalobutyl ether of formula

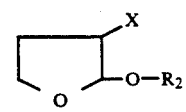   (II)

in which X is halogen and $R_2$ is unsubstituted or halo-substituted $C_1$-$C_{10}$alkyl, $C_3$-$C_6$-cycloalkyl that is unsubstituted or substituted by halogen, $C_1$-$C_4$alkyl or by $C_1$-$C_4$alkoxy, or phenyl or benzyl each of which is unsubstituted or substituted by halogen, $C_1$-$C_4$alkyl, $C_1$-$C_4$alkoxy, nitro or cyano, and
b) then reacting the compound of formula III with an aqueous bisulfite solution to form a bisulfite adduct of formula

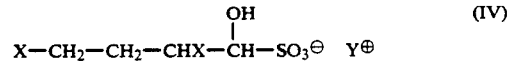   (IV)

in which X is halogen and Y is a cation equivalent of an alkali metal or alkaline earth metal ion, and
c) then cyclising the adduct, in the presence of a base, with a thiolate of formula

   (V)

in which $R_1$ is $C_1$-$C_4$alkyl or benzyl and Z is a cation equivalent of an alkali metal or alkaline earth metal ion, to form a cyclopropanecarbaldehyde of formula I.

Process steps a), b) and c) are novel. The invention relates to the combination of all three process steps, as described hereinbefore, to the combination of the process steps a)+b), and b)+c), and to the individual steps a), b) and c) on their own.

The 1,2,4-trihalobutyl ethers of formula III and the bisulfite adducts of formula IV are also novel and the present invention relates to those also.

The invention thus relates to the novel 1,2,4-trihalobutyl ethers of formula

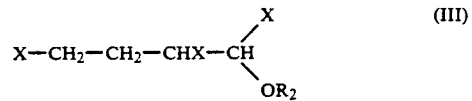   (III)

in which X is halogen and $R_2$ is unsubstituted or halo-substituted $C_1$-$C_{10}$alkyl, $C_3$-$C_6$-cycloalkyl that is unsubstituted or substituted by halogen, $C_1$-$C_4$alkyl or by $C_1$-$C_4$alkoxy, or phenyl or benzyl each of which is unsubstituted or substituted by halogen, $C_1$-$C_4$alkyl, $C_1$–$C_4$alkoxy, nitro or cyano, and to the novel bisulfite adducts of formula

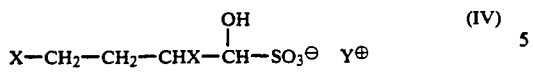

in which X is halogen and Y is a cation equivalent of an alkali metal or alkaline earth metal ion.

The tetrahydrofurans of formula II are valuable starting compounds for the process according to the invention. Some of these compounds are known from the literature. The compounds of formula II can be prepared analogoulsy to processes known from the literature. The alcoholysis of 2,3-dihalotetrahydrofurans [M. Holik et al.; (Chem. Zvesti; 25 (1971), 9); V. Zezula and M. Kratochvil; Collect. Czech. Chem. Commun.; 35 (1970), 1745], [L. M. Bolotina et al.; Khim. Geterotsikl. Soedin; 4 (1968), 200], for example, provides a convenient route to this class of compounds. The Zn- or $ZnCl_2$-catalysed addition of oxiranes to 2,3-dichlorotetrahydrofuran or mixtures of 2,3-dichlorotetrahydrofuran with tetrahydrofuran is another convenient method of producing 2-[2- or 4-chloroalkyl-substituted]-3-chlorotetrahydrofurans of formula II [M. Kratochvil, Collect. Czech. Chem. Commun. 25 (1960), 1353].

The invention also relates to the novel tetrahydrofurans of formula II

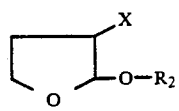

in which X is halogen and $R_2$ is unsubstituted or halo-substituted $C_1$–$C_{10}$alkyl, $C_3$–$C_6$-cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, with the proviso that when X is chlorine $R_2$ is not unsubstituted $C_1$–$C_6$alkyl, cyclohexyl, $C_4$–$C_{10}$alkyl substituted in the 2 position by chlorine, or 4-chlorobutyl, and that when X is bromine or iodine $R_2$ is not $C_1$–$C_4$alkyl.

The individual Process Steps of the invention, and combinations thereof, are defined as follows:

Two-step processes:

The process for the preparation of cyclopropanecarbaldehydes of formula

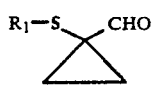

in which $R_1$ is $C_1$–$C_4$alkyl or benzyl, which comprises b) reacting a 1,2,4-trihalobutyl ether of formula

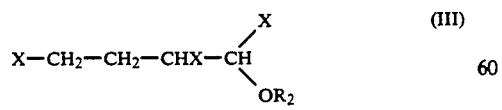

in which X is halogen and $R_2$ is unsubstituted or halo-substituted $C_1$–$C_{10}$alkyl, $C_3$–$C_6$cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, with an aqueous bisulfite solution to form a bisulfite adduct of formula

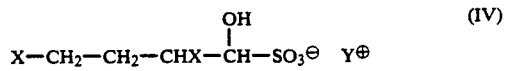

in which X is halogen and Y is a cation equivalent of an alkali metal or alkaline earth metal ion and
c) subsequently cyclising the adduct, in the presence of a base, with a thiolate of formula

in which $R_1$ is $C_1$–$C_4$alkyl or benzyl and Z is a cation equivalent of an alkali metal or alkaline earth metal ion, to form a cyclopropanecarbaldehyde of formula I;

and the process for the preparation of a bisulfite adduct of formula

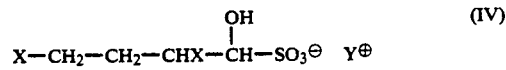

in which X is halogen and Y is a cation equivalent of an alkali metal or alkaline earth metal ion, which comprises
a) reacting a tetrahydrofuran of formula

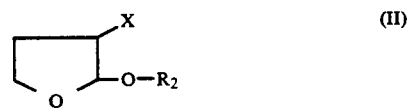

in which X is halogen and $R_2$ is unsubstituted or halo-substituted $C_1$–$C_{10}$alkyl, $C_3$–$C_6$cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, with a halogenating agent to form a 1,2,4-trihalobutyl ether of formula

in which X is halogen and $R_2$ is unsubstituted or halo-substituted $C_1$–$C_{10}$alkyl, $C_3$–$C_6$cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, and
b) then reacting the compound of formula III with an aqueous bisulfite solution to form the bisulfite adduct of formula IV.

SINGLE-STEP PROCESSES

The process for the preparation of 1,2,4-trihalobutyl ethers of formula

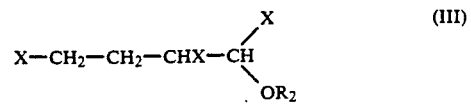

in which X is halogen and $R_2$ is unsubstituted or halo-substituted $C_1$–$C_{10}$alkyl, $C_3$–$C_6$cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, which comprises
a) reacting a tetrahydrofuran of formula

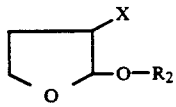
(II)

in which X is halogen and $R_2$ is unsubstituted or halo-substituted $C_1$–$C_{10}$alkyl, $C_3$–$C_6$cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, with a halogenating agent;
the process for the preparation of a bisulfite adduct of formula

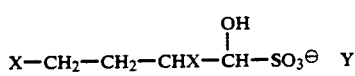
(IV)

in which X is halogen and Y is a cation equivalent of an alkali metal or alkaline earth metal ion, which comprises
b) reacting a 1,2,4-trihalobutyl ether of formula

(V)

in which X is halogen and $R_2$ is unsutstituted or halo-substituted $C_1$–$C_{10}$alkyl, $C_3$–$C_6$cycloalkyl that is unsubstituted or substituted by halogen, $C_1$–$C_4$alkyl or by $C_1$–$C_4$alkoxy, or phenyl or benzyl each of which is unsubstituted or substituted by halogen, $C_1$–$C_4$alkyl, $C_1$–$C_4$alkoxy, nitro or cyano, with an aqueous bisulfite solution;
and the process for the preparation of cyclopropanecarbaldehydes of formula

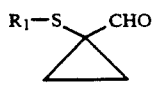
(I)

in which $R_1$ is $C_1$–$C_4$alkyl or benzyl, which comprises
c) cyclising a bisulfite adduct of formula

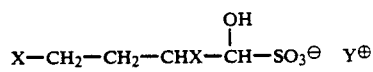
(IV)

in which X is halogen and Y is a cation equivalent of an alkali metal or alkaline earth metal ion, in the presence of a base, with a thiolate of formula

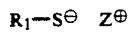
(V)

in which $R_1$ is $C_1$–$C_4$alkyl or benzyl and Z is a cation equivalent of an alkali metal or alkaline earth metal ion, to form a cyclopropanecarbaldehyde of formula I.

In the definitions used in this description, the generic terms used have especially the following individual meanings:

Alkyl is methyl, ethyl, n-propyl, isopropyl, n-butyl, isobutyl, sec-butyl or tert-butyl, or an isomeric pentyl, hexyl, heptyl, octyl, nonyl or decyl radical. Where $R_2$ is alkyl, $C_1$–$C_4$alkyl is preferred.

Halogen is fluorine, chlorine, bromine or iodine, especially chlorine or bromine.

Alkali metal and alkaline earth metal ions are especially lithium, sodium, potassium and also the divalent ions of magnesium and calcium. In the case of the bisulfite adducts the sodium and potassium salts are preferred, with the sodium salts being more especially preferred.

Haloalkyl as a meaning of the substituent $R_2$ is especially 2-chloroethyl, 2-chloropropyl, 2-chlorobutyl or 4-chlorobutyl.

Cycloalkyl is cyclopropyl, cyclobutyl, cyclopentyl or cyclohexyl, preferably cyclopentyl or cyclohexyl. The cycloalkyl radicals may in turn be substituted by halogen, alkyl or alkoxy. Preferably, the cycloalkyl radicals are unsubstituted or are substituted by up to three identical or different substituents from halogen, $C_1$–$C_4$alkyl and $C_1$–$C_4$alkoxy.

$R_2$ as phenyl or benzyl is preferably unsubstituted, but can also be substituted by up to three identical or different substituents from halogen, $C_1$–$C_4$alkyl, $C_1$–$C_4$alkoxy, nitro and cyano. $R_2$ as alkyl is preferably unsubstituted $C_1$–$C_4$alkyl.

In the case of the two-step or the three-step process (combination of Process Steps b)+c); a)+b); or a)+b)+c)) the syntheses may advantageously be carried out as "one-pot processes", that is to say without isolation of the respective intermediates.

The following features have proved advantageous for the individual Process Steps:

PROCESS STEP A)

The halogenation of the tetrahydrofuran II is carried out successfully in the presence of from 0.005 to 0.5 mol of a catalyst, optionally with from 0.0001 to 0.5 mol of a proton donor, from 1 to 6 mol of the halogenating agent and from 0 to 200 ml of an inert solvent per mol of educt. Suitable proton donors are, for example, water, alcohols, acids, such as hydrochloric acid, sulfuric acid, carboxylic acids and sulfonic acids, and ammonium ions (with the exception of quaternary ammonium ions). Preferred proton donors are water, alcohols and hydrochloric acid. In an especially advantageous manner, Process Step a) is carried out without a solvent in the presence of from 0.02 to 0.1 mol of a catalyst, optionally with from 0.001 to 0.01 mol of water, and from 1.10 to 1.15 mol of halogenating agent.

Especially preferred are those halogenating agents of which the residue can be removed from the reaction mixture easily owing to their ready volatility, such as, for example, thionyl chloride or thionyl bromide. Thionyl chloride is particularly suitable.

There may be mentioned as catalysts especially aromatic amines, such as pyridine, lutidine, 4-dimethylaminopyridine, quinoline, picoline, tertiary amines, such as N,N-dimethylaniline, 4-N',N'-dimethylaminopyridine or 1,4-diazabicyclo[2.2.2]octane, and also trialkylamines, such as triethylamine or ethyldiisopropylamine, or amides, such as dimethylformamide, dimethylacetamide or hexamethylphosphorus triamide.

Suitable solvents are, inter alia, aromatic hydrocarbons, such as toluene, xylene or benzene; ethers, such as tetrahydrofuran, dioxane, diethyl ether or diisopropyl ether; alicyclic or aliphatic hydrocarbons, such as cyclohexane, hexane or higher-boiling alkanes; chlorinated hydrocarbons, such as dichloromethane or trichloromethane.

The process is preferably carried out at temperatures of from room temperature to approximately 140° C., especially in a range of from 30° to 100° C. and more especially from 80° to 85° C.

In an especially preferred form, the process is carried out at the boiling temperature of the reaction mixture in the presence of from 0.02 to 0.1 mol of pyridine or triethylamine as catalyst, from 1.10 to 1.15 mol of thionyl chloride, and without a solvent. In this advantageous form of Process Step a), the product obtained is a 1,4-dichloro-2-halobutyl ether of formula

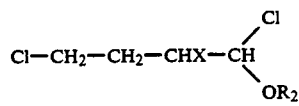
(IIIa)

in which X is halogen and $R_2$ is unsubstituted or halo-substituted $C_1$-$C_{10}$alkyl, $C_3$-$C_6$cycloalkyl that is unsubstituted or substituted by halogen, $C_1$-$C_4$alkyl or by $C_1$-$C_4$alkoxy, or phenyl or benzyl each of which is unsubstituted or substituted by halogen, $C_1$-$C_4$alkyl, $C_1$-$C_4$alkoxy, nitro or cyano.

PROCESS STEP B)

The hydrolysis of the ether III to form the bisulfite adduct IV is advantageously carried out in an aqueous two-phase system under controlled pH conditions. When using a 40% sodium bisulfite solution, in particular the following preferred and especially preferred ratios of solvents and educts come into consideration:

Preferred are from 1.0 to 2.0 mol of sodium bisulfite (in the form of a 40% aqueous solution), from 20 to 200 ml of water and from 20 to 200 ml of an inert organic solvent per mol of ether III. Especially preferred are from 1.0 to 1.1 mol of sodium bisulfite (in the form of a 40% aqueous solution), from 40 to 60 ml of water and from 40 to 60 ml of organic solvent per mol of ether III.

The reaction is advantageously carried out at temperatures of from 0° to 100° C., and preferably at temperatures of from 30° to 80° C.

The pH value of the reaction mixture is maintained in a range of approximately from 2 to 7, preferably from 3.0 to 3.5, by the controlled addition of a base. NaOH or KOH (for example in the form of a 30% aqueous solution) are suitable as bases.

Preferably, an ether of formula IIIa is used for carrying out Process Step b).

The solvents suitable for Process Step b) correspond to those mentioned in Step a). In addition, esters such as, for example, ethyl acetate, are suitable. Toluene is especially preferred.

The bisulfite adduct obtainable by Process Step b) can be obtained in a simple manner by first of all gently heating the reaction mixture and removing the organic phase at that elevated temperature. The product IV crystallises from the aqueous phase in a high degree of purity and can either be separated off, or directly further processed in Process Step c) in the form of an aqueous suspension.

PROCESS STEP C)

The bisulfite adduct IV is suspended in from 400 to 1000 ml, preferably from 600 to 800 ml, of water per mol of educt, or the suspension obtainable in accordance with Process Step b) is used directly. At temperatures of from −20° to +40° C., preferably from 0° to 5° C., from 1.0 to 1.5 mol, preferably from 1.0 to 1.05 mol, of thiolate V are added thereto. The reaction mixture is adjusted to a basic pH value with from 1.02 to 2.20 mol, preferably from 1.02 to 2.0 mol, of sodium hydroxide solution. The product can then be extracted from the reaction mixture.

For carrying out Process Step c), bisulfite adducts of formula

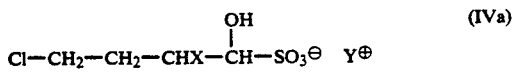

in which X is halogen and Y is a cation equivalent of an alkali metal or alkaline earth metal ion are especially preferred.

Preferred thiolates are the sodium and potassium thiolates of formula V.

Apart from sodium hydroxide solution, other alkali metal and alkaline earth metal hydroxides or carbonates may be used as bases in the afore-mentioned Reaction Steps b) and c).

The process according to the invention is distinguished by numerous advantages as compared with that known from the prior art. It uses readily available educts and reagents. Carrying out the reaction is uncomplicated (temperature, solvents, pH control, the use of water as reaction medium, isolation of the products, good removal of the by-products and residues etc.). The process can be carried out with or without isolation of the intermediates. The bisulfite adduct IV is stable in storage. In addition, the process has a high yield and high product quality in every single reaction step.

The following Examples illustrate the invention.

PREPARATORY EXAMPLES

P.1. Preparation of (1,2,4-trichlorobut-1-yl)-methyl ether 130.9 g (1.1 mol) of thionyl chloride are added dropwise at from 80° to 85° C., over a period of 2 hours, to 136.5 g (1.0 mol) of 3-chloro-2-methoxytetrahydrofuran and 1.58 g (0.02 mol) of pyridine, evolution of gas occurring immediately. The reaction mixture is further stirred until the evolution of gas has ceased, and is then cooled to room temperature.

185.7 g (97%) of the title compound of formula

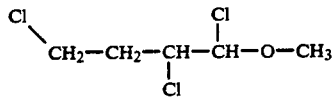

are isolated in the form of a light-brown liquid (Comp. No. 1.01).

Spectroscopic data for compound No. 1.01:

| ppm | Identification |
| --- | --- |
| 1.9–2.9 | multiplet 2H—C(3) |
| 3.4–4.0 | multiplet 2H—C(4) |
| 3.63 | singlet $H_3C$—O |
| 4.1–4.6 | multiplet H—C(2) |
| 4.68 and 4.76 | 2 doublets, ratio 1:2, J = 7 and J = H—C(1) |

MS: 157(10), 155(16), 121(2), 119(7), 107(3), 105(10), 94(2), 92(5), 81(34), 79(100), 55(3), 53(5), 51(13); M=191.5; (for both diastereoisomers).

The compounds of Table I can be prepared analogously (using SOCl₂ or SOBr₂ as halogenating agent).

TABLE I

Compounds of formula $$X'-CH_2-CH_2-CHX''-CH(X''')-OR_2 \quad (III)$$

| Comp. No. | X' | X'' | X''' | R₂ | B.p./pressure | Yield |
|---|---|---|---|---|---|---|
| 1.01 | Cl | Cl | Cl | CH₃ | +100° C./5.3 Pa | 97% |
| 1.02 | Br | Cl | Br | CH₃ | | |
| 1.03 | Br | Br | Br | CH₃ | | |
| 1.04 | Cl | Br | Cl | CH₃ | +85° C./2.7 Pa | 96.8% |
| 1.05 | Cl | Cl | Cl | C₂H₅ | | |
| 1.06 | Br | Cl | Br | C₂H₅ | | |
| 1.07 | Br | Br | Br | C₂H₅ | | |
| 1.08 | Cl | Br | Cl | C₂H₅ | | |

P.2. Preparation of the bisulfite adducts IV

P. 2.1. Preparation of the bisulfite adduct of 2,4-dichlorobutyraldehyde 185.6 g (0.97 mol) of (1,2,4-trichlorobut-1-yl)-methyl ether are added dropwise at from 40° to 45° C., over a period of one hour, to 310.0 g (1.0 mol) of a 33.5% aqueous sodium hydrogen sulfite solution and 50 ml of toluene. At the same time the pH value is maintained at from 3.0 to 3.5 with 30% aqueous NaOH solution. The reaction mixture is then heated to from 70° to 75° and the toluene phase is removed and discarded. The product crystallises out on cooling the aqueous phase to 15° C.

162.1 g (66%) of the title compound of formula

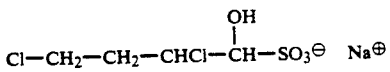

$$Cl-CH_2-CH_2-CHCl-\underset{|}{\overset{OH}{CH}}-SO_3^\ominus \; Na^\oplus$$

are isolated in the form of a colourless powder (Comp. No. 2.01).

By recrystallisation of the mother liquors it is possible to isolate a further 58.2 g (23.7%) of the title compound.

P. 2.2. Preparation of the bisulfite adduct of 2,4-dichlorobutyraldehyde from 3-chloro-2-methoxytetrahydrofuran (II)

P. 2.2.1. Using triethylamine as catalyst 13.1 g (110 mmol) are added dropwise at from 80° to 85° C., over a period of 2 hours, to 13.6 g (100 mmol) of 3-chloro-2-methoxytetrahydrofuran and 0.2 g (2 mmol) of triethylamine. The (1,2,4-trichlorobut-1-yl)-methyl ether obtainable in this manner is added over a period of 30 minutes at from 40° to 45° C. to 31.0 g (100 mmol) of a 33.5% aqueous sodium hydrogen sulfite solution and 6 ml of toluene, the pH value of the reaction mixture being held at from 3.0 to 3.5 with 30% NaOH solution. The reaction mixture is then heated to from 70° to 75° C., the toluene phase is removed and the aqueous phase is cooled to room temperature, the product precipitating.

68.3 g (94.8%) of the title compound of formula

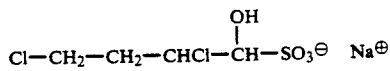

$$Cl-CH_2-CH_2-CHCl-\underset{|}{\overset{OH}{CH}}-SO_3^\ominus \; Na^\oplus$$

are isolated in the form of a 34% aqueous suspension (Comp. No. 2.01).

P. 2.2.2. Using lutidine as catalyst

Analogously to Example P. 2.2.1., 66.1 g (91.7%) of the title compound of formula

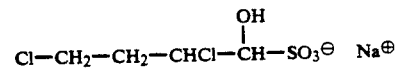

$$Cl-CH_2-CH_2-CHCl-\underset{|}{\overset{OH}{CH}}-SO_3^\ominus \; Na^\oplus$$

in the form of a 34% aqueous bisulfite adduct suspension (Comp. No. 2.01) are obtained from 13.6 g (100 mmol) of 3-chloro-2-methoxytetrahydrofuran, 0.1 g (2 mmol) of lutidine and 13.1 g (110 mmol) of thionyl chloride, 31.0 g (100 mmol) of 33.5% aqueous sodium bisulfite solution and 6 ml of toluene.

¹H-NMR (360 MHz, D₂O): δ=2.1–2.45 and 2.5–2.65 (2m, 2H-C(3)); 3.7–3.95 (m, 2H-C(4)); 4.55–4.9 (3 complex signals, H-C(1) and H-C(2)).

The compounds of Table II are obtained analogously to the P.2. Preparatory Examples.

TABLE II

Compounds of formula $$X'-CH_2-CH_2-\underset{|}{\overset{X''}{CH}}-\underset{|}{\overset{OH}{CH}}-SO_3^\ominus \; Na^\oplus$$

| Comp. No. | X' | X'' | Yield [%] |
|---|---|---|---|
| 2.01 | Cl | Cl | 95 |
| 2.02 | Br | Cl | |
| 2.03 | Br | Br | |
| 2.04 | Cl | Br | 90⁽¹⁾ |

⁽¹⁾from 3-bromo-2-methoxytetrahydrofuran with SOCl₂ as halogenating agent and pyridine as catalyst.

P. 3. Preparation of the cyclopropanecarbaldehydes I

P. 3.1. 1-methylthiocyclopropanecarbaldehyde 42.8 g (175 mmol) of 2,4-dichlorobutyraldehyde bisulfite adduct (suspended in 200 ml of water) are added dropwise at from 0° to 5° C., over a period of one hour, to 98.5 g (225 mmol) of a 16% aqueous sodium methyl thiolate solution and 60.0 g (450 mmol) of a 30% aqueous sodium hydroxide solution. The mixture is stirred for a further 45 minutes and then 100 ml of dichloromethane are added and the aqueous phase is separated off. The organic phase is concentrated by evaporation in vacuo (50° C./500 mbar) in a rotary evaporator.

19.4 g (95.6%) of the title compound of formula

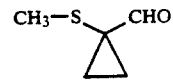

(Compound No. 4.01) are isolated.

The compounds of Table III are isolated in an analogous manner.

TABLE III

| Example | Educt | R₁S⊖Na⊕ | Product | Yield |
|---|---|---|---|---|
| P.3.1.2. | BrCH₂—CH₂CHClCHSO₃Na (with OH) | CH₃SNa | CH₃—S–△–CHO | |

TABLE III-continued

| Example | Educt | R₁S⊖Na⊕ | Product | Yield |
|---|---|---|---|---|
| P.3.1.3. | ClCH₂CH₂CH(Br)—CH(OH)SO₃Na | CH₃SNa | CH₃—S—C(CHO)(cyclopropane) | 90% |
| P.3.1.4. | BrCH₂CH₂CH(Br)—CH(OH)SO₃Na | CH₃SNa | CH₃—S—C(CHO)(cyclopropane) | |
| P.3.1.5. | ClCH₂CH₂CH(Cl)—CH(OH)SO₃Na | CH₃(CH₂)₃SNa | CH₃(CH₂)₃—S—C(CHO)(cyclopropane) | 69% |
| P.3.1.6. | ClCH₂CH₂CH(Cl)—CH(OH)SO₃Na | C₆H₅—CH₂SNa | C₆H₅—CH₂—S—C(CHO)(cyclopropane) | 58% |

P. 3.2. 1-methylthiocyclopropanecarbaldehyde from 3-chloro-2-methoxytetrahydrofuran without isolation of the intermediates 273.0 g (2.0 mol) of 3-chloro-2-methoxytetrahydrofuran, 3.16 g (40 mmol) of pyridine, 261.8 g (2.2 mol) of thionyl chloride, 620 g (2.0 mol) of 33.5% of aqueous sodium hydrogen sulfite solution and 100 ml of toluene are reacted analogously to Example P.2.2. to form an aqueous suspension of the 2,4-dichlorobutyraldehyde bisulfite adduct. The aqueous suspension obtainable in this manner is diluted with 210 ml of water and cooled to 0° C. 876.3 g (2.0 mol) of a 16% sodium methylate solution and 533.0 g (4.0 mol) of a 30% aqueous sodium hydroxide solution are then added dropwise over a period of 3 hours at from 0° to 5° C. The mixture is then stirred for a further 45 minutes at from 0° to 5° C., heated to room temperature, extracted with toluene or dichloromethane, the aqueous phase is separated off and the organic phase is concentrated in vacuo in a rotary evaporator.

185.7 g (80%) of the title compound of formula

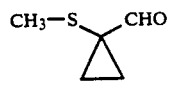

(Comp. No. 4.01) are isolated.

The compounds of Table IV can be prepared analogously to the above Preparatory Examples:

TABLE IV

Compounds of formula $$R_1-S\diagdown\diagup CHO \quad (I)$$
(cyclopropane)

| Comp. No. | R₁ | Boiling point/pressure | Yield |
|---|---|---|---|
| 4.01 | CH₃ | +91 to +92° C./10000 Pa | 80% |
| 4.02 | CH₃(CH₂)₃— | | 61% |
| 4.03 | C₆H₅—CH₂— | +90 to +91° C./1.3 Pa | 51% |
| 4.04 | C₂H₅ | +57 to +58° C./1800 Pa | |
| 4.05 | C₃H₇-n | +74 to +76° C./2000 Pa | |
| 4.06 | C₃H₇-i | +67 to +68° C./2000 Pa | |

What is claimed is:

1. Bisulfite adducts of formula

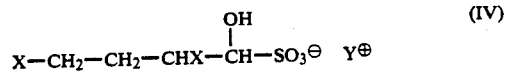

in which X is halogen and Y is an alkali metal or alkaline earth metal ion.

2. Bisulfite adducts of formula

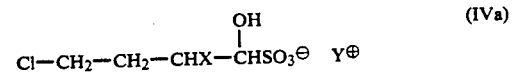

in which X is halogen and Y is an alkali metal or alkaline earth metal ion.

* * * * *